United States Patent [19]

Sandhage et al.

[11] 4,077,406
[45] Mar. 7, 1978

[54] PELLET IMPLANTER FOR ANIMAL TREATMENT

[75] Inventors: Ellsworth Roland Sandhage, Pearl River; Arthur Sinclair Taylor, Spring Valley, both of N.Y.

[73] Assignee: American Cyanamid Company, Stamford, Conn.

[21] Appl. No.: 699,739

[22] Filed: Jun. 24, 1976

[51] Int. Cl.² .............................................. A61M 5/18
[52] U.S. Cl. .................................... 128/217; 128/264
[58] Field of Search .................... 128/217, 264; 124/45

[56] References Cited

U.S. PATENT DOCUMENTS

| 2,620,796 | 12/1952 | Eriksen et al. | 128/217 |
| 3,402,712 | 9/1968 | Eisenhand | 128/217 |
| 3,774,607 | 11/1973 | Schmitz | 128/217 |

FOREIGN PATENT DOCUMENTS 840,276    7/1960    United Kingdom ................ 128/217

*Primary Examiner*—Dalton L. Truluck
*Attorney, Agent, or Firm*—Charles F. Costello, Jr.

[57] ABSTRACT

A pellet implanter for the subcutaneous implantation of one or more spherical or cylindrical pellets of a total size of up to about 1/8 inch by 1 inch (3 mm × 25 mm) through a hypodermic needle uses a transparent compact flat cartridge having parallel feed chambers permitting visual observation of the feed and 360° rotation of the cartridge holder with respect to the pistol grip and plunger assembly. A collet holds a replaceable injection needle which permits injection of therapeutic agents in repository form beneath the skin of animals for therapeutic and/or growth control purposes.

2 Claims, 7 Drawing Figures

PELLET IMPLANTER FOR ANIMAL TREATMENT

BACKGROUND OF THE INVENTION

It has long been known that various substances affect the health and/or rate of growth of mammals. In the animal husbandry industry it is desirable that various substances be implanted beneath the skin of an animal to affect the rate of growth of the animal or to control other characteristics. For instance, antibiotics can be injected to control diseases, or hormones may be injected to increase the weight or enhance the characteristics of the meat. It has been considered desirable that any substances injected be injected in the ear or neck or other portion of the subject animal at such location as to minimize effects on useful meat and minimize the likelihood that a person eating meat from the animal would ingest whatever material had been implanted. Various growth influencing substance may be used depending upon the animal or the effect desired.

Hormones such as diethyl stilbestrol have been implanted in chickens for instance where the material has the effect of caponizing a rooster, with improved production of tender meat.

The present implantation device is designed for use with any solid pellets, or materials which may be incorporated with a carrier as a solid pellet, for injection beneath the skin of the subject domestic animal.

PRIOR ART

U.S. Pat. No. 2,620,796 — Eriksen and White — Dec. 9, 1952 — PELLET INJECTOR — shows a clip fed hypodermic type injector, with provisions for the control of the depth of penetration, in which a loop type handle at the end of the plunger is used for the control of the plunger, which as it slides forward picks up pellets from a clip of channel shaped configuration having an open slot through which the pellet may be viewed.

U.S. Pat. No. 2,883,984 — Candido and Miskel — Apr. 28, 1959 — PELLET IMPLANTER — shows a piston grip type implanter with a hollow hypodermic needle in which an elongated plunger slides through a card to pick up pellets which are carried through the hypodermic needle into a subject. This patent discloses the implantation of pellets into beef cattle at the base of the ear and certain advantages of a piston grip hypodermic injector. The disclosure of this patent is hereby herein incorporated by this reference thereto.

U.S. Pat. No. 3,402,712 — Eisenhand — Sept. 24, 1968 — PELLET IMPLANTER — shows a piston grip type implanter with a hypodermic needle and a plunger, which upon actuation by a trigger member causes pellets from a vertical pellet conduit to be fed into the path of the plunger and forced through the hypodermic needle into the subject. The plunger of this implanter releases only when there is a pellet in the chamber ready for implanting, so that the user is certain there is a pellet present to be implanted if the trigger operates. There is also a sight hole to permit visual inspection of the pellet in the load position.

U.S. Pat. No. 3,538,916 — Wiles & Groff — Nov. 10, 1970 — INJECTION PISTOL — shows a sear released spring loaded plunger with adjustable depth control means, in which the pellet is loaded into the front of the needle at the time of use.

U.S. Pat. No. 3,774,607 — Schmitz — Nov. 27, 1973 — PELLET IMPLANT GUN — shows a pistol type implant gun using a long throw plunger which operates through pellet cylinders in a circular magazine. The line of travel of the plunger through the magazine is opened to observation so that the user can check that the cylinder of the cartridge is aligned and that the cylinder actually contains pellets. Flexible fingers retain the pellets within the cylinders until time of use.

Australian Pat. No. 228,022 — Needham and Thorne — accepted Apr. 12, 1960 — HYPODERMIC IMPLANTER, shows a circular magazine having chambers for the implantation of pellets through a hypodermic needle but uses a pair of circular finger grips and a operating knob at the back end of the plunger in alignment with the plunger for forcing of the plunger through the magazine and the hypodermic needle at the time of implantation of the pellet.

SUMMARY OF THE INVENTION

It has now been found that pellets may be implanted under the skin of domestic animals with a particularly convenient lightweight economical type of injection gun.

Solid pellets containing antibiotics, hormones, anabolic growth regulants or other therapeutic agents may be implanted under the skin of domestic animals to control the growth rate or other characteristics. Such materials are well known. Some materials may be injected as a liquid or suspended in a liquid but the rate of dissolution or reaction is apt to be undesirably fast. Some materials may be implanted as a pellet, but conveniently many materials are incorporated in a carrier such as castor wax, beeswax or a delayed release matrix such as a polyester resin containing glycolic acid ester linkages which are subject to hydrolytic degradation to tissue compatible components, or other types of matrices in which the medicament is released at a desired rate. For injection in animals it is frequently desired that the material be injected in the neck or in an ear so that the site of the injection is not subject to human consumption, if the animal is used as a food product.

The present gun is lightweight, and thin, so that a magazine having a series of chambers therein may be flat and of relatively small size, and fed into a C-shaped magazine receiver which may be rotated through 360° with respect to the main frame having a pistol grip so that either a right or a left handed person may rotate the magazine in its receiver to such a position that the feeding of the magazine through the magazine receiver is in a direction most convenient for the particular operator, having reference to the animal being treated, and the restraining system used to restrain the animal at the time of injection.

Obviously, the animal is apt to express displeasure in being stuck and suitable restraints are required so that the operator may most accurately inject the pellet at a desired location, with a minimum of risk of misplacement, or injury to the operator or the animal during the procedure. The present pellet implanter is particularly small and convenient with respect to its capacity, so that comparatively large implants may be injected with a minimum of effort. Additionally, the implanter is relatively simple and readily cleaned so that even if it dropped to the ground at the scene of operations or covered with hair or blood from the injected animal it may be readily cleaned for subsequent use.

While not limited thereto, it is convenient for the gun to handle one or more pellets and a total size of up to about ⅛th of an inch by 1 inch through a hypodermic needle.

The pellets may be cylindrical, with a sufficient number of cylinders to completely fill the magazine pellet chambers, or partially fill the magazine pellet chambers for a smaller dose; the pellets may be spherical with as many spherical pellets in each magazine pellet chamber as are needed for a desired dose, up to the capacity of the magazine pellet chamber.

It is desirable that the needle and the size of the pellet or pellets be as small as is consistent with the desired dosage. The present implanter is particularly convenient because smaller lengths of pellets for smaller dosage may be implanted using the same magazine containers and gun. A sleeve may be placed around the plunger in the gun, with a shorter needle for smaller implants. These and other advantages of the present pellet implanter are obvious from the following description of one embodiment thereof.

Figure 1:
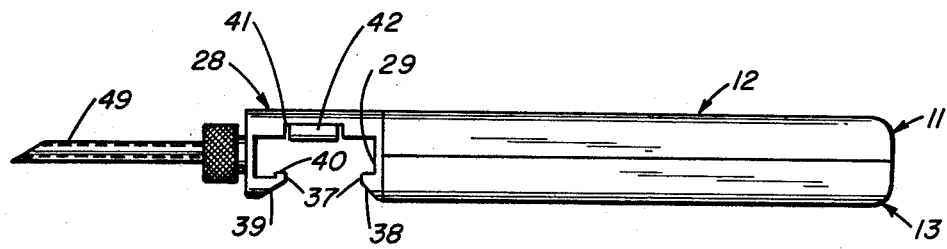
FIG. 1 shows the top view of the assembled implanter without a cartridge in place.
Figure 2:
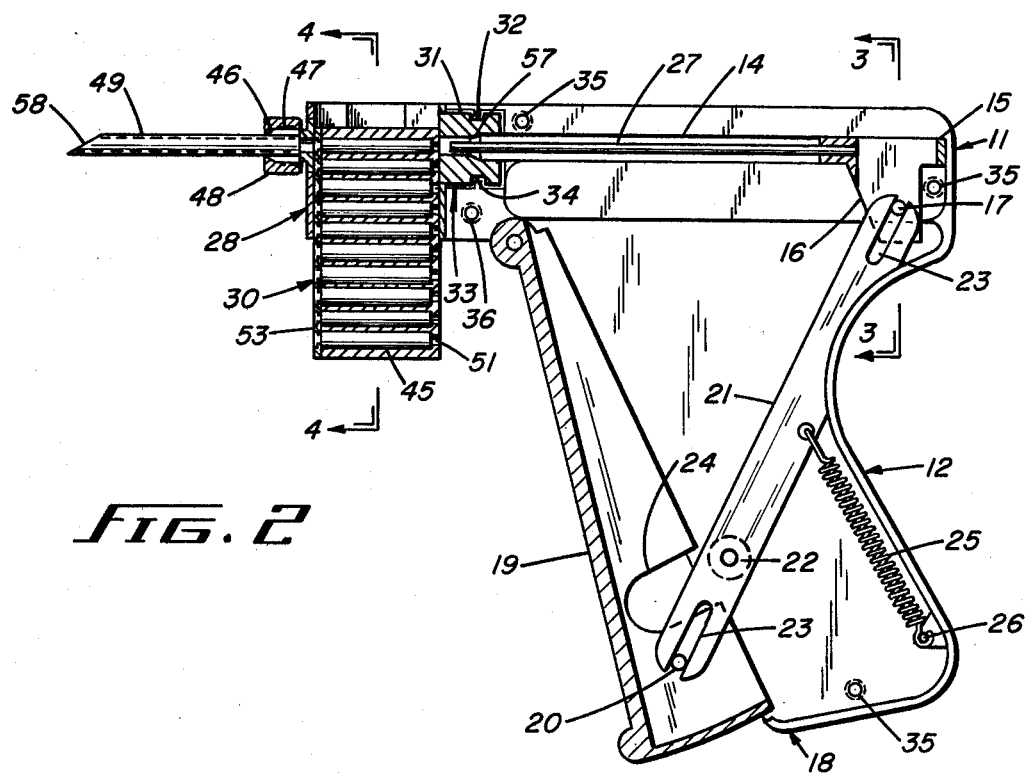
FIG. 2 is a side view in partial section of the implanter with a cartridge in position.
Figure 3:
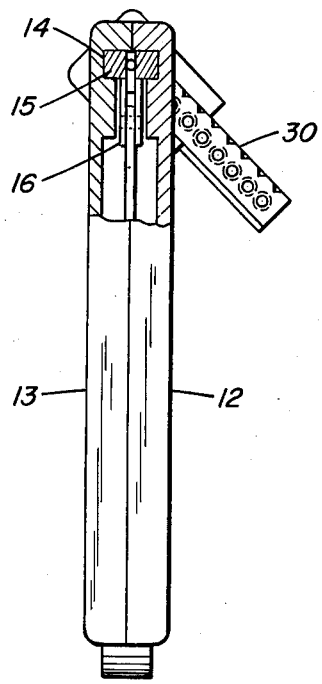
FIG. 3 is a rear view in partial section of the implanter showing the magazine receiver tilted at about 45°.

The pellet implanter has a main frame 11 conveniently consisting of a back case 12 and face case 13. Conveniently these are essentially symmetrical and each of one piece. If desired the back case can be deeper and the face case in effect merely a plate on top. Whereas described as of one piece each, as are many of the other items in the present assembly, it is to be understood that if because of manufacturing convenience in a particular machine shop it may be desirable to make the parts of two or more pieces which are welded, riveted or otherwise assembled to each other. These are spoken of as functionally integral.

In the main frame, both in the front and back case, is a plunger slide groove 14 in which is mounted for reciprocating motion a plunger slide 15. The plunger slide has a T-shaped configuration with the head sliding in the plunger slide groove 14 and controlled as to orientation and direction that by this groove, and with a pair of operating bars 16 extended downward between which bars is an operating pin 17.

Extending downward on the main frame is a pistol grip 18 near the front part of which is hinged an operating trigger 19. Conveniently the operating trigger 19 is full length for full hand motion control. Near its lower end is a trigger pin 20. As shown the operating trigger 19 is of U-shaped configuration so that the trigger pin 20 is internal thereof. A connecting link 21 is pivoted on a link pin 22 and extends between the operating pin 17 and the trigger pin 20, with a link slot 23 at each end of the link so that as the operating trigger 19 is depressed it rotates and in turn rotates the connecting link 21 with a mechanical multiplication causing the plunger slide 15 to move forward a greater distance, than the stroke length of the operating trigger 19. A clearance slot 24 in the operating trigger permits rearward motion of the operating trigger so that a full stroke of the connecting link 21 moves the plunger slide 15 forward for substantially the length of the main frame in the plunger slide groove 14.

A biasing spring 25 extends between the connecting link 21 and a spring pin 26 in the pistol grip, to retract the connecting link, and with it reset the operating trigger and the plunger slide when the operating trigger is released.

Other mechanical movements may be used to transmit trigger movement to the plunger slide.

Extending from the front of the plunger slide 15 is a plunger 27. The plunger extends towards the front of the main frame 11 and is of such a length that on full retraction of the plunger slide, the front of the plunger is behind the magazine feed slot 29 in the magazine 30, as described below.

On full extension the plunger slides forward far enough to eject the one or more solid pellets 52 in the chamber 45 in the magazine.

At the front of the main frame is a C-shaped magazine receiver 28. The magazine receiver is of generally C-configuration and has therein a magazine feed slot 29. The magazine feed slot 29 is of generally rectangular configuration to receive a magazine 30.

The magazine receiver 28 has at its rear end a cylindrical boss 31 having therein a retaining groove 32.

In the front of the main frame is a hollow cylindrical magazine receiver clamping sleeve 33 having therein a retaining ring 34. The retaining ring 34 fits into the retaining groove 32 on the cylindrical boss 31 so that the cylindrical boss is free to rotate on slight loosening of the hollow cylindrical magazine receiver clamping sleeve 33. On additional loosening the boss will slide out of the sleeve permitting disassembly. Assembly screws 35 hold the two cases of the main frame together; and a sleeve clamping screw 36 permits clamping of the hollow cylindrical magazine receiver clamping sleeve 33. By slightly loosening the screws adjacent to the boss, the magazine receiver may be rotated for 360° around the front end of the main frame to permit alignment of the magazine receiver, for the convenience of the operator.

The magazine receiver 28 is of generally rectangular configuration with two lips adjacent to an open face 37 of the magazine feed slot 29. A rear lip 38 extends over and holds the back part of the magazine 30. The front lip 39 holds the front part of the magazine 30 and has a slighter greater spacing so that the magazine can be designed to be slightly thicker at the front thereby controlling orientation. The front lip 39 may extend over the front of the magazines and have a slight locking lip 40 to further aid in controlling orientation.

By having the magazine of such shape that the magazine can be inserted into the magazine feed slot in only one orientation, the risk of the user putting the magazine in backwards or upside down is minimized.

Figure 4:
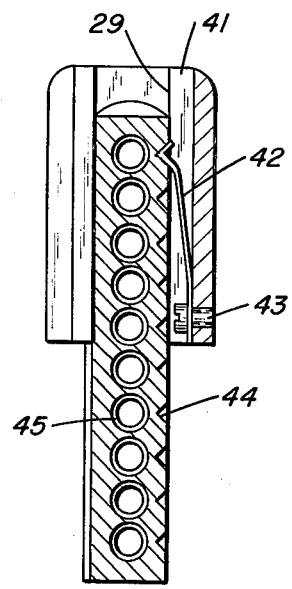
FIG. 4 is a sectional view along section line 4—4 of FIG. 2 showing a magazine in the C-shaped magazine receiver, positioned by a detent.
Figure 5:
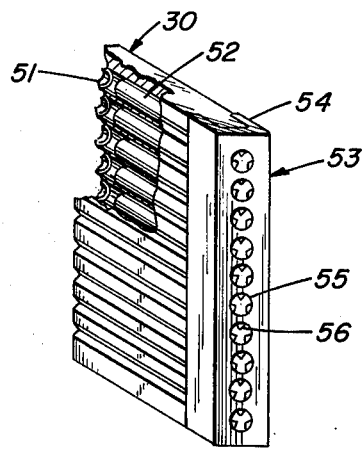
FIG. 5 is a pictorial view, partially broken away, showing one magazine having a series of pellet chambers containing cylindrical implant pellets.

At the back of the magazine feed slot 29 is a positioning detent slot 41 in which is a detent spring 42, as shown in FIG. 4, which is held by a detent spring screw 43. The detent spring 42 locks into a groove 44 in the magazine when the magazine is in proper position. The detent spring 42 serves to control linear positioning of the magazine 30 and insure that the chamber 45 is coaxial with the plunger 27 at the time of operation of the trigger.

At the front face of the magazine receiver 28 is a hypodermic needle holding collet 46 consisting of the usual collet fingers 47 which are clamped by the usual collet ring 48 against the hypodermic needle 49.

The collet fingers 47 may be integral with the magazine receiver 28, but conveniently are on separate collet sleeve 50—as too often the collet ring is accidentally clamped against the collet fingers without a needle being in place, which bends and mutilates the fingers. A separate replaceable collet sleeve permits convenient replacement, and also different size sleeves permit using different size hypodermic needles.

The magazine 30 itself is a flat multichambered insert, preferably transparent and having therein a series of uniformly spaced parallel chambers 45 for the pellets 52. At the rear end of each chamber is a concentric restriction 51. This constriction is large enough to admit the plunger 27 but it is small enough to retain a pellet 52 in the chamber. Each chamber may hold one or more pellets 52. The number and size of pellets is controlled by the optimum size for injection of a particular material into a particular subject animal and depends upon the characteristics of the injected material. Those dose may be molded into one or more pellets for consecutive injection into the subject animal. It may be convenient, for instance, to have four pellets each about ⅛th of an inch diameter by ¼ inch long for a maximum load; with 1, 2 or 3 pellets being used for smaller dosage in otherwise identical magazines. Smaller pellets may be used in smaller animals.

At the other end of the chambers is a cover clip 53 which is a snap or friction fit for easy assembly over the front of the magazine.

The cover clip 53 has a thickened corner 54 which fits into the front lip 39 in the magazine receiver 28 and may be held by the locking lip 40 so that the magazine having a cover clip thereon can only be inserted with one orientation into the magazine receiver.

Additionally, the cover clip has molded therein a series of discharge apertures 55, each generally large enough for the discharge of the pellets in the chamber, but having formed therein flexible pellet-retaining leaves 56. These leaves 56 are sufficiently thin and flexible that they may be easily displaced on injection of a pellet but are sufficiently rigid to retain the pellets in position during shipment and storage and until the time of injection.

Molded in the backside of the magazine 30 are a series of grooves 44. Each groove is of a size and shape to engage the detent spring 42 when the magazine is in a properly aligned position.

The alignment is such that the plunger 27, the funnel shaped plunger orifice 57 in cylindrical boss, and the hypodermic needle 49 in the collet 46 are coaxial and in alignment with the chamber 45 in a magazine 30 in the magazine receiver 28 at the time of injection of a pellet into a domestic animal.

As indicated above, one or more pellets, not necessarily of the same size may be conveniently stored in each of the chambers 45 until time of injection. The number of chambers and the size of chambers in a magazine may be varied depending upon therapeutic requirements. A smaller size chamber may be used. A smaller size plunger may conveniently be used with a smaller size hypodermic needle, if the subject and the therapeutic requirements so indicate. A slightly conical entrance to the magazine and a smaller plunger can be adapted readily to the assembly without having to modify other parts.

If it is desired to use a shorter stroke with a shorter hypodermic needle, a short section of tube may be placed over the plunger 27 to restrict and control the length of its stroke.

Usually it is desirable that the plunger upon operation of the trigger 19 extend far enough that the end of the plunger is very close to the bevel 58 on the hypodermic needle 49.

It is also convenient to put a shield on the front of the hypodermic needle to control the depth of injection, if it cannot be readily controlled by eye or if the subject animal is unruly.

Figure 6:
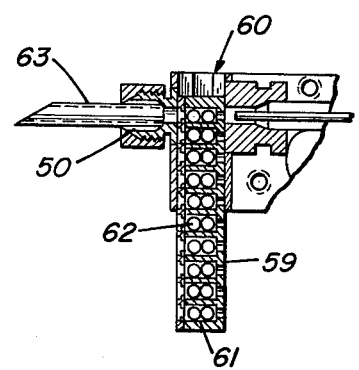
FIG. 6 is a side view in partial section of the magazine and magazine receiver, similar to FIG. 2, but with shorter magazine chambers for reduced capacity.

FIG. 6 shows a modification having a compact magazine 59 in a compact magazine receiver 60. This compact magazine is interchangeable in the hollow cylindrical magazine receiver clamping sleeve 33; and has short chambers 61 for one or two spherical pellets 62. A short hypodermic needle 63 may be used. The shorter needle and spherical pellets are convenient for smaller doses of medicament, and smaller animals. The choice of needle size and lengths, and site and amount of material injected may vary over a wide range depending upon the desires of the user, for a specific situation.

The magazine can be designed with grooves in both faces, and a symmetrical clip, so that the magazine can be introduced from the top or bottom of the magazine feed slot 29, and with an interchangeable top and bottom of the magazine. Using one axis and two planes of symmetry is convenient for insertion. With such construction both faces of the magazine should be transparent to permit visual inspections of chamber contents. The top and bottom of the magazine are convenient areas for product designation with this construction.

At the time of use, the individual operator selects one or more magazines containing pellets, depending upon the number of animals to be injected, and makes arrangements for the animals to be confined on their movement restricted, as for example by an animal chute or a tie-down, then adjusts the angle of the magazine receiver to the main frame to that most convenient, tightens the assembly screws 35 and sleeve clamping screw 36, then proceeds to insert a hypodermic needle and inject one or more pellets from the magazine into the subject domestic animal.

It is convenient, but not necessary, that either the magazine itself 30 or the cover clip 53 by color coded as to dosage and material so that the user can immediately spot by color magazines having interchangeable contents. Similarly, the magazines may have a label attached thereto or may have embossed on one face such information as may be of value to the user. Usually a group of magazines will be packaged in a protective box giving suitable protection for storage, and complete instructions. For some materials it will be necessary that the contents of the box be merely clean, others clean and sterile, and for some protection may be required against ambient moisture or oxygen.

Theoretically, at least, if the cover clip fits on by a snap fit, it can be unsnapped and the magazine reloaded however it is usually preferable to use new magazines of a disposable type, to permit the advantages of factory loading by the manufacturer and to guarantee that maximum standardization of dosage levels be obtained.

Figure 7:
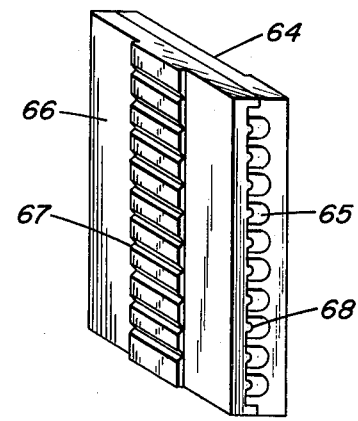
FIG. 7 is a pictorial view of a modified magazine construction.

FIG. 7 shows an alternative magazine construction in which a magazine face 64 is molded with U-shaped chambers 65, and the open U-shaped chambers closed by a magazine cover 66, which has detent grooves 67 therein. Retaining leaves 68 are molded in the magazine cover 66. The magazine is the functional equivalent of the magazine having a cylindrical chamber 45, but easier to mold of plastic. Even if the chambers 45 have a slight taper, drilling or molding may be more expensive than using U-shaped chambers.

The choice depends upon available molding equipment, and loading convenience.

The magazine cover may be either a friction fit, or adhesively united. Usually adhesively uniting is preferred as it prevents reloading with the wrong pellets.

Other modifications and changes within the scope of the following claims suggest themselves to those skilled in the art.

We claim:

1. A pellet implanter for implanting at least one solid pellet in a selected location beneath the skin of a domestic animal comprising:

a two-piece main frame having a functionally integral pistol grip, a plunger slide groove in said main frame, a reciprocating plunger slide sliding in said plunger slide groove, a plunger fixed with relationship to said plunger slide which plunger is retractable into said main frame and extendable from the front of said main frame, an operating trigger pivotally attached to said main frame, a connecting link means between said operating trigger and said plunger slide to move the plunger slide forward on pulling the trigger, a biasing spring to move the plunger slide rearwardly on release of the trigger, and a hollow cylindrical magazine receiver clamping sleeve, having a retaining ring, in the front of the main frame;

a C-shaped magazine receiver, having therein a magazine feed slot which is adapted to receive and hold a magazine, said slot being generally rectangular, but having one corner larger than the others and thereby adapted to receive a magazine in only one orientation, said magazine feed slot having lips adapted to hold a magazine in location and having a gap between the lips adapted to expose the major portion of one face of a magazine, a cylindrical boss, having a retaining groove, integral with the magazine receiver, which boss fits into and is held by said clamping sleeve, said retaining ring and said retaining groove permitting rotation of the magazine receiver with respect to the main frame on slight loosening of the clamping sleeve, and complete disassembly on further loosening of the clamping sleeve, a positioning detent in the magazine receiver adapted to control the movement of a magazine along its axis, a hypodermic needle holding collet on the other side of the magazine receiver, and a hypoderic needle in said collet, the plunger, the clamping sleeve, the cylindrical boss, the collet and the hypodermic needle being coaxial, and adapted to be in alignment with a pellet chamber in a magazine in the magazine receiver.

2. The pellet implanter of claim 1 having in the magazine receiver a flat multichambered magazine, said magazine comprising a flat transparent magazine, having therein a series of uniformly spaced parallel chambers, each chamber having therein at least one solid pellet adapted for implantation into a domestic animal, and at the end of each chamber adjacent to the pistol grip, a concentric restriction, of such size as to admit the plunger, but small enough to retain the pellet in the chamber, and at the other end of the chambers, a cover clip that fits over the end of the multichambered cartridge, having coaxial with each chamber a pellet discharge aperture large enough to permit the discharge of the pellets, but having flexible pellet retaining leaves in said discharge aperture to retain each pellet in the chamber until positively displaced by movement of the plunger, said clip having one enlarged face to cooperate with the magazine feed slot, so that the magazine enters with the magazine feed slot in only one orientation, and a series of grooves in the magazine to cooperate with the positioning detent and index the magazine for the discharge of each pellet, in turn, through the hypodermic needle.

* * * * *